United States Patent [19]

Saito et al.

[11] Patent Number: 5,128,376

[45] Date of Patent: * Jul. 7, 1992

[54] METHOD FOR PERCUTANEOUSLY ADMINISTERING PHYSIOLOGICALLY ACTIVE AGENTS USING AN ADJUVANT A SOLVENT AND A DIOL MODERATOR

[75] Inventors: Kenichiro Saito; Jorge Heller; Wilfred A. Skinner, all of Menlo Park, Calif.

[73] Assignee: Nitto Denko Corporation, Osaka, Japan

[*] Notice: The portion of the term of this patent subsequent to Aug. 12, 2003 has been disclaimed.

[21] Appl. No.: 577,831

[22] Filed: Sep. 4, 1990

Related U.S. Application Data

[63] Continuation of Ser. No. 218,413, Jul. 12, 1988, abandoned, which is a continuation of Ser. No. 824,395, Jan. 23, 1986, abandoned, which is a continuation-in-part of Ser. No. 510,100, Jul. 1, 1983, abandoned.

[51] Int. Cl.⁵ .................. A61K 47/22; A61K 47/14; A61K 47/10
[52] U.S. Cl. .................. 514/772; 514/785; 514/947; 514/788
[58] Field of Search ............... 514/947, 724, 777, 785

[56] References Cited

U.S. PATENT DOCUMENTS

| | | | |
|---|---|---|---|
| 4,038,417 | 7/1977 | Nelson | 514/772 |
| 4,039,664 | 8/1977 | Stoughton et al. | 514/947 |
| 4,440,777 | 4/1984 | Zupan | 424/274 |
| 4,605,670 | 8/1986 | Saito et al. | 514/619 |

FOREIGN PATENT DOCUMENTS

| | | | |
|---|---|---|---|
| 43738 | 1/1982 | European Pat. Off. | 514/947 |
| 1518683 | 7/1978 | United Kingdom . | |

*Primary Examiner*—Jacqueline Stone
*Attorney, Agent, or Firm*—Sughrue, Mion, Zinn Macpeak & Seas

[57] ABSTRACT

A method of percutaneously administering a physiologically active agent which comprises applying to the skin of a mammal a physiologically active agent in a carrier system which comprises at least one adjuvant, at least one solvent and at least one diol and/or triol moderator. The adjuvant can be selected from aliphatic hydrocarbons, halogen substituted aliphatic hydrocarbons, alcohol esters of aliphatic carboxylic acids, mono- or di-ethers, ketones, higher monoalcohols or mixtures thereof. The solvent can be selected from thioglycerols, lactic acid and esters thereof, cyclic ureas, compounds represented by the general formula $R_1R_2NCONR_3R_4$, pyrrolidone-type compounds, amides, lactones or mixtures thereof.

25 Claims, 1 Drawing Sheet

FIG. 1

IN VITRO DIAZEPAM FLUX
THROUGH RAT SKIN
AT 30 C. DRUG CONCENTRATION
2.5% IN 1 ml RESERVOIR

A. 25% $C_{12}Cl$ in DMAc
B. 25% $C_{12}Cl$ in 1:1 MIXTURE OF DMAc/2,3-BUTANEDIOL
C. 25% $C_{12}Cl$ in 1:2 MIXTURE OF DMAc/2,3-BUTANEDIOL
D. 25% $C_{12}Cl$ in 2,3-BUTANEDIOL

FIG. 2

METHOD FOR PERCUTANEOUSLY ADMINISTERING PHYSIOLOGICALLY ACTIVE AGENTS USING AN ADJUVANT A SOLVENT AND A DIOL MODERATOR

CROSS REFERENCE TO RELATED APPLICATION

This is a continuation of application Ser. No. 07/218,413 filed Jul. 12, 1988, now abandoned, which is a continuation of application Ser. No. 06/824,395 filed Jan. 23, 1986, now abandoned which is a continuation-in-part of application Ser. No. 510,100 filed Jul. 1, 1983, now abandoned, by Saito et al and entitled METHOD FOR PERCUTANEOUSLY ADMINISTERING PHYSIOLOGICALLY ACTIVE AGENTS USING AN ADJUVANT, A SOLVENT AND A DIOL MODERATOR.

BACKGROUND OF THE INVENTION

1. Field of the Invention

The present invention relates to a method for accelerating the percutaneous absorption of a physiologically active agent (hereafter often merely an "active agent" for brevity).

2. Description of the Prior Art

Active agents are commonly administered to the skin or mucosal tissues to treat local problems and systemic administration of active agents is commonly accomplished by ingesting pills or by injections. However, recently attempts have been made to achieve systemic administration of active agents by topical applications to the skin or mucosal tissues. Such topical means of achieving systemic administration has the advantage that desired blood levels can be readily achieved and maintained so that duration of therapy can be readily controlled. Thus, side effects due to an overdose of the active agent can be prevented. Also, metabolism due to a first pass through the liver and gastric disturbances, which are characteristic of certain drugs such as indomethacin when administered orally, can also be eliminated.

However, normal skin is relatively impermeable to most therapeutic agents in that desired blood levels of the therapeutic agent cannot be achieved by means of percutaneous absorption. The percutaneous absorption of therapeutic agents can, however, be enhanced by means of adjuvants or penetration enhancers.

One of the best known of such penetrating adjuvants is dimethyl sulfoxide, the use of which is described in detail in U.S. Pat. No. 3,551,554 Herschler et al, which patent broadly suggests the use of dimethyl sulfoxide as a penetrating adjuvant for psychopharmacological drugs such as benzodiazepine derivatives.

British Patent 1,504,302 Brooker et al deals with sedative methods and compositions and discloses the administration of sedatives by applying to the skin of a non-human animal a sedating amount of one or more sedative compounds in various penetrating adjuvants such as hydrocarbons such as aromatic hydrocarbons or paraffins, halogenated aliphatic hydrocarbons, ketones, esters, ethers, alcohols, amides or sulfones. Brooker et al broadly indicates that one or more of the above liquids can be used in combination, but exemplify the halogenated aliphatic hydrocarbons only with carbon tetrachloride and exemplify the amides only with dimethylformamide.

Japanese Patent Application 52-148,614 (unexamined) Yonemushi discloses, without supporting data or explanation of substance, the use of sulfones by-produced in the refining of petroleum "as solvents to enhance the efficacy of drugs for skin disease" and "as drug penetration enhancers".

U.S. Pat. No. 4,202,888 Eckert et al discloses absorbable pharmaceutical compositions comprising at least one cardiac glycoside distributed in a vehicle comprising an absorption-enhancing amount of at least a partial glyceride of a fatty acid of medium chain length.

U.S. Pat. No. 3,472,931 Stoughton relates to percutaneous absorption using lower alkyl amides, and exemplifies binary systems which comprise dimethylacetamide and ethanol, dimethylacetamide and isopropyl alcohol and dimethylacetamide and isopropyl palmitate. Stoughton does not exemplify or disclose the combination of dimethylacetamide with higher molecular weight alcohols or lower molecular weight esters.

U.S. Pat. No. 4,017,641 DiGiulio deals with skin moisturizing compositions comprising 2-pyrrolidones which can be used with suitable oils and waxes including aliphatic straight chain fatty acids and alcohols of from about 10 to about 20 carbon atoms. This patent does not, however, deal with percutaneous administration of physiologically active agents.

European Patent Application 0043738 discloses binary percutaneous administration systems which comprise a monoglyceride, a diol or a diol ether in combination with a second component such as an alcohol, ester, amide or the like.

The present invention involves multicomponent carrier systems for the percutaneous administration of physiologically active agents which differ from the systems disclosed in the above prior art.

SUMMARY OF THE INVENTION

Per the present invention, it has been discovered that certain multicomponent carrier systems provide enhanced and controlled percutaneous administration of physiologically active agents.

The carrier systems of the present invention comprise at least one adjuvant (Component A), at least one solvent (Component B) and at least one diol and/or triol moderator.

The adjuvants of the present invention are selected from aliphatic hydrocarbons or halogen substituted aliphatic hydrocarbons, alcohol esters of aliphatic carboxylic acids, mono- or di-ethers, ketones, higher aliphatic monoalcohols or mixtures thereof. It is necessary that the adjuvant of the present invention have a melting point below 38° C.

The solvents of the present invention are selected from thioglycerols, lactic acid or esters thereof, cyclic ureas, compounds represented by the general formula $R_1R_2NCONR_3R_4$, pyrrolidone-type compounds, amides, lactones or mixtures thereof.

Per the present invention, a physiologicaly active agent can be percutaneously administered by blending the same with a combination of Component A, Component B and a diol and/or triol moderator and applying the same to the skin.

The above-described compositions can be used as bases for medical preparations comprising active agents applicable to the outer skin.

One object of the present invention is to provide base compositions or percutaneous absorption enhancing combinations of Component A, Component B and a diol and/or triol moderator (often abbreviated as PAEC or PAECs hereafter) for medical preparations for external use which enhance the permeability of active agents through the skin and the percutaneous absorption of active agents.

A second object of the present invention is to provide pharmaceutical compositions comprising a PAEC for external use which provides good permeability of active agents through the skin and percutaneous absorption of active agents.

A third object of the present invention is to provide a method for enhancing the permeability of active agents through the skin and percutaneous absorption of active agents using a PAEC per the present invention.

In a preferred embodiment, the combination of the present invention which enhances percutaneous absorption comprises one or more members selected from the group consisting of certain pyrrolidone-type compounds and amides and mixtures thereof, one or more members selected from the group consisting of certain alkyl halides, fatty acid esters, higher aliphatic monoalcohols, aliphatic hydrocarbons and mixtures thereof and one or more diol and/or triol moderators.

A fourth object of the present invention is to provide PAECs which ensure rapid and controlled transepidermal delivery of physiologicaly active agents in man or other animals.

A fifth object of the present invention is to provide such rapid and controlled transepidermal delivery which provides drug blood levels in the therapeutic range for the treatment of humans and other animals.

A sixth object of the present invention is to provide, through transepidermal delivery, at appropriately adjusted rates, relatively constant therapeutic blood levels so as to avoid the side effects and reduced therapeutic effects that may result from wide fluctuations in blood levels over time.

DESCRIPTION OF THE PREFERRED EMBODIMENTS

Examples of Component A include the following compounds.

(1) Straight, branched or cyclic aliphatic hydrocarbons having 5 to 24 carbon atoms which may be substituted with one or more halogens.

As halogen substituents, bromine and chlorine are preferred with chlorine being most preferred.

Straight or branched hydrocarbons having 5 to 24 (preferably 6 to 18) carbon atoms can be used which may be saturated or unsaturated with preferably 1 to 2 unsaturated bonds. In the case of cyclic hydrocarbons, 6 to 10 membered mono- or 10 to 12 membered dicyclic hydrocarbons are preferred and such may be substituted with saturated or unsaturated alkyl groups having 1 to 4 carbon atoms such as methyl, butyl, isopropenyl, etc.

Specific examples include n-pentane, n-hexane, n-heptane, n-octane, n-nonane, n-decane, n-undecane, n-dodecane, n-tetradecane, n-hexadcane, n-octadecane, 2-methylpentane, 2-methylhexane, 2,3-dimethylhexane, 2-methylnonane, 2,6-dimethyloctane, 2,2,4,4,6,8,8-heptamethylnonane, pristane, limonene, hydrogenated limonene dimer, cyclohexane, 1,3--dimethylcyclohexane, cyclooctane, isobutyl-cyclohexane, cyclododecane, methyldecaline, decaline, octyl chloride, decyl chloride, dodecyl chloride, hexadecyl chloride, dodecyl bromide, dichlorododecane, etc.

(2) Alcohol esters of aliphatic carboxylic acids having a total number of carbon atoms of from 7 to 18, preferably 7 to 17:

As the alcohol moiety, monovalent alcohols having 1 to 6 carbon atoms such as methyl alcohol, ethyl alcohol, n-propyl alcohol, iso-propyl alcohol, n-butyl alcohol, iso-butyl alcohol, sec-butyl alcohol, t-butyl alcohol, n-amyl alcohol, iso-amyl alcohol, n-hexyl alcohol, etc., are preferred. Further, as the carboxylic acid moiety, fatty acids having 6 to 16 carbon atoms are preferred and saturated fatty acids having 8 to 14 carbon atoms are most preferred. Specific examples of such esters include methyl laurate, ethyl laurate, butyl laurate, isopropyl myristate, etc.

(3) Mono- or di-ethers having 10 to 18 carbon atoms:

Specifically, there are alkyl monoethers such as dihexyl ether, dioctyl ether, methoxydodecane, ethoxydodecane, etc., ethers having an alicyclic group such as 1,8-cineole, etc., alkyl diethers such as ethylene glycol dibutyl ethers, ethylene glycol dioctyl ethers, etc.

(4) Ketones having 10 to 18 carbon atoms:

Aliphatic ketones having 11 to 15 carbon atoms are preferred, examples of which include 2-undecanone, 3-undecanone, 4-undecanone, 5-undecanone, 6-undecanone, 2-dodecanone, 4-dodecanone, 5-dodecanone, 7-tridecanone, etc.

(5) Higher aliphatic monalcohols having from 8 to 26 carbon atoms which may be branched, straight chain, saturated, unsaturated or cyclic and which may be primary, secondary or tertiary.

Examples of Component B include the following compounds:

(1) Thioglycerols:

Any mono-, di- and trithioglycerols can be used, an example of which includes α-monothioglycerol.

(2) Lactic acid and esters thereof:

As the alcohol moiety in the esters, monovalent aliphatic alcohols having 1 to 4 carbon atoms are preferred, specific examples of which include lactic acid, methyl lactate, ethyl lactate, butyl lactate, etc.

(3) Cyclic ureas:

5-Membered or 6-membered rings are preferred, specific examples of which include ethylene urea, N,N-dimethylethylene urea and the corresponding propylene ureas, etc.

(4) Compounds represented by the general formula:

wherein $R_1$, $R_2$, $R_3$ and $R_4$ each represents a hydrogen atom, a lower alkyl group having 1 to 4 carbon atoms (methyl, ethyl, n-propyl, iso-propyl, n-butyl, etc.) or an acyl group having 1 or 2 carbon atoms:

Specific examples thereof include urea, N-methylurea, N-ethylurea, N-butylurea, 1,1-dimethylurea, 1,3-dimethylurea, 1,1,3,3-tetramethylurea, N-acetyl-N'-methylurea, etc.

(5) Compounds represented by the general formula:

wherein $R_5$ represents a hydrogen atom or a lower alkyl group having 1 to 4 carbon atoms (methyl, ethyl, n-propyl, iso-propyl, etc.), $R_6$ represents a hydrogen atom or a lower alkyl group having 1 to 4 carbon atoms and n represents an integer of 3 to 5:

Specific examples thereof include 2-pyrrolidone, N-methyl-pyrrolidone, N-methylpiperidone, caprolactam, N-methylcaprolactam, etc.

(6) Compounds represented by the general formula:

wherein $R_7$ represents a hydrogen atom or an alkyl group having 1 to 3 carbon atoms (methyl, ethyl, n-propyl, etc.) and $R_8$ and $R_9$ each represents an alkyl group having 1 to 3 carbon atoms, with the proviso that $R_7$, $R_8$ and $R_9$ have in total at least 3 carbon atoms:

Specific examples thereof include N,N-diethyl formamide, N,N-dimethylacetamide, N,N-diethylacetamide, N,N-dimethylpropionamide, N,N-diethylpropionamide, etc.

(7) Lactones having 4 to 6 carbon atoms:

Specific examples thereof include γ-butyrolactone, δ-valerolactone, etc.

As earlier indicated, a diol and/or triol moderator is used in combination with the active agent and Components A and B of the present invention.

The diol and/or triol can be straight or branched chain. If desired, or necessary, one or more diols can be used, one or more triols can be used and one or more diols can be used in combination with one or more triols.

The diols and triols can have up to 8 carbon atoms. Diols appear to provide better results in controlling the rate of drug absorption through the skin than triols having the same carbon number as the diols when a Component A having more than 15 carbon atoms is used in the combination.

The diols and triols appear to give essentially similar results when the system contains a Component A with 10 to 15 carbon atoms in the combination, although with a Component A with 10 carbon atoms with some active agents, triols seem to provide slightly better results whereas with a Component A with 15 carbon atoms with some active agents diols seem to provide slightly better results. The effect noted is that 10 to 15 carbon atoms appear to be a transition point with triols providing better results as the number of carbon atoms in Compound A decreases below 10 and with diols providing better results as the number of carbon atoms in Component A increases above 15. The triols appear to provide better results than the diols when a Component A having less than 10 carbon atoms is used in the combination.

It is not generally preferred to use a combination of a diol(s) and a triol(s) where Component A has more than 18 carbon atoms or less than 8 carbon atoms. Preferred diols and triols have 3 to 8 carbon atoms and the most preferred diols and triols are aliphatic and have 3 to 6 carbon atoms. The most preferred triol is glycerol.

Examples of diols include, e.g., aliphatic diols such as 1,2-propane diol, 1,3-butane diol, 2,3-butane diol, 1,5-pentane diol, 1,6-hexane diol, etc.

The diol(s) and triol(s) can be used in any proportion.

The amount of diol and/or triol moderator used is not unduly limited, but is typically on the order of about 10 to about 400 weight percent, more preferably about 25 to about 200 weight percent, based on the weight of solvent Component B. The resulting combination of materials must, of course, be liquid.

The diol and/or triol moderator reduces the activity of Components A and B of the present invention which provides a means of further controlling the rate of active agent absorption.

Greater amounts of diol and/or triol moderator decrease the rate of active agent flux while lesser amounts of diol and/or triol moderator increase the rate of active agent flux as compared to greater amounts.

It is to understand that the diol and/or triol moderator does not enhance percutaneous absorption per the present invention, rather, in all amounts it reduces the rate of percutaneous absorption, which effect has not been suspected in the art.

In addition to the above, there are certain most preferred PAECs per the present invention, and these are discussed below.

We are unsure why the most preferred combination of PAECs of the present invention offers enhanced percutaneous absorption; however, the data we have generated indicate that there is a synergistic effect between Components A and B which can be appropriately moderated, as desired, by varying the amount of diol and/or triol moderator.

We consider the materials such as the pyrrolidone-type compounds and amides to basically serve a solvent function and materials such as the alkyl halides, fatty acid esters, higher aliphatic monoalcohols and aliphatic hydrocarbons to serve as adjuvants which enhance the solvating function of the solvent. We further believe that the solvents carry the active agent whereas the adjuvants open up the stratum corneum. We do not wish to be bound by these theories, and we merely use the terminology "solvent" and "adjuvant" to maintain a line of distinction between the two classes of materials which are mandatorily used in combination.

The most preferred adjuvants as Component A of the present invention include one or more members selected from the group consisting of alkyl halides, fatty acid esters, higher aliphatic monoalcohols, aliphatic hydrocarbons and mixtures thereof.

Of the alkyl halides, those having from 8 to 18 carbon atoms are most preferred, with chloride being the preferred halogen. Both alkyl bromides and iodides are potentially useful, but alkyl bromides and alkyl iodides tend to be unstable. Alkyl fluorides are also useful.

The alkyl moiety may be straight or branched chain, may be cycloaliphatic or unsaturated, e.g., alkanes and alkenes are useful.

Most preferred alkyl halides are later exemplified.

The aliphatic hydrocarbons most preferably have 10 to 18 carbon atoms. They may be straight or branched chain and may be cycloaliphatic or unsaturated, e.g., alkanes and alkenes are useful.

The fatty acid esters are conveniently represented by the formula $R_{10}COOR_{11}$, $R_{10}$ representing the acid moiety and $R_{11}$ representing the alcohol moiety. It is most preferred that the total number of carbon atoms in $R_{10}$ and $R_{11}$ be from 10 to 17.

$R_{10}$ and $R_{11}$ may be linear, branched, saturated, unsaturated.

Preferred higher monoalcohols are the aliphatic monoalcohols with from 8 to 24 carbon atoms and most preferred are those with 12 to 20 carbon atoms. The aliphatic monoalcohols may be branched chain, straight chain, saturated, unsaturated or cyclic.

The most preferred solvents as Component B include the pyrrolidone-type compounds and the amides.

The pyrrolidones are most preferably alkyl pyrrolidones of the formula:

where $R_{12}$ is an alkyl group containing up to 4 carbon atoms, $R_{13}$ is a hydrogen atom and n is 3 to 5.

The amides are most preferably represented by the formula:

where $R_{14}$ can be hydrogen or an alkyl group with up to 3 carbon atoms and $R_{15}$ can be an alkyl group with up to 3 carbon atoms and $R_{16}$ can be hydrogen or an alkyl group with up to 3 carbon atoms, with the proviso that $R_{14}$ to $R_{16}$ contain at least 3 carbon atoms in total.

The base compositions of the present invention can be prepared by dissolving Component A in Component B and then mixing the diol and/or triol moderator therein. The order of mixing is not important. The amount of Component A to be used is generally from 0.1 to 80% by weight based on the total weight of Components A and B, preferably 0.5 to 50% by weight. Preferred proportions of the diol and/or triol moderator have earlier been given. Of course, pharmaceutically acceptably additives such as water, etc., can also be added to the base compositions.

The pharmaceutical compositions for topical application per the present invention can be prepared by blending active agents with the above-described composition. There is no particular limit on the active agents used so long as the active agents are systemically active and percutaneously applicable.

Specific examples of active agents include benzodiazepines (e.g., Diazepam, Nitrazepam, Flunitrazepam, Lorazepam, Fludiazepam, Clonazepam), diuretic agents [e.g., thiazides (e.g., Bendroflumethiazide, Polythiazide, Methyclothiazide, Trichloromethiazide, Cyclopenthiazide, Bentylhydrochlorothiazide, Hydrochlorothiazide, Bumetanide)], anithypertensive agents (e.g., Clonidine), anithistamic agents [e.g., aminoethers (e.g., diphenhydramine, Carbinoxamine, Diphenylpyraline), ethylenediamines (e.g., Fenbenzamine), monoamines (e.g., Chlorophenylamines)], non-steroid antiinflammatory agents (e.g., Indomethacine, Ibuprofen, Ibufenac, Alclofenac, Diclofenac, Mefenamic acid, Flurbiprofen, Flufenamic acid, Ketoprofen), anti-tumor agents (e.g., 5-fluorouracil, 1-(2-tetrahydrofuryl)-5-fluorouracil, Cytarabine, Floxuridine). Steroid antiinflammatory agents (e.g., Cortisone, Hydrocortisone, Prednisolone, Predonisone, Triamcinolone, Dexamethasone, Betamethasone), antiepileptic agents (e.g., Ethosuximide), antiarrythmic agents (e.g., Ajmalin, Purajmalin, Pindolol, Propranolol, Quinidine), psychotropic agents [e.g., Clofluperol, Trifluperidol, Haloperidol, Moperone), scopolamines (e.g., methyl scopolamine, butyl scopolamine), metoclopramide, cleboprid, chlorpromazine, atropines (e.g., methyl atropine bromide, methylanisotropine bromide), vascular dilating agents (e.g., isosorbide dinitrate, nitroglycerine, pentaerythritol tetranitrate, propanyl nitrate, dipyridamole), antibiotics, e.g., tetracylines (e.g., Tetracyline, Oxytetracycline, metacycline, doxycyline, Minocycline), chloramphenicols, erythromycines], anti-asthmatic agents (e.g. theophylline), calcium slow channel blockers (e.g., nifedipine, verapamil), etc. The method of the present invention can also be utilized to percutaneously administer peptides such as LH-RH, insulin and the like. Of course, pharmaceutically acceptable salts such as the hydrochloride, sodium, potassium, hydrobromide, etc., salts can be used.

Since the present invention is of particular application with respect to the benzodiazepine materials, these are discussed in more detail below. Particularly preferred benzodiazepine materials are those which illustrate the benzodiazepine skeleton as schematically illustrated as follows:

wherein X is Cl, Br, or $NO_2$ and Y is with varying degrees of unsaturation and substitution at positions 1, 2, 3, 4, and 5 as follows a) 1, 2 and 4, 5 are unsaturated: $R_1$ and $R_3$ are H; $R_2$ is (R is H or $CH_3$) and N—Z is N→O.

b) 1, 2 are saturated and 4, 5 are unsaturated: $R_3$ is H or OH; —$R_2$ is —H or =O or =N*; $R_1$ is or CH$_2$—CH$_2$—N(C$_2$H$_5$)$_2$ or R$_1$ is C(R)=N* (R is H or CH$_3$) and is joined to R$_2$ via "*" (a single bond) as follows:

c) 1, 2 and 4, 5 are saturated: R$_1$ is H; —R$_2$ is =O; R$_3$ is H and positions 4 and 5 constitute a second ring system as follows:

where R and R$^1$ are H and CH$_3$.

Specific examples of benzodiazepines which can be percutaneously administered using the active ingredient/penetration adjuvant combinations of the present invention include:

a) Chlordiazepoxide; 7-Chloro-2-methylamino-5-phenyl-3H-1, 4-benzodiazepine-4-oxide
b) Diazepam; 7-Chloro-1,3-dihydro-1-methyl-5-phenyl-2H-1,4-benzodiazepine-2-one
c) Oxazepam; 7-Chloro-1,3-dihydro-3-hydroxy-5-phenyl-2H-1,4-benzodiazepine-2-one
d) Temazepam; 7-Chloro-1,3-dihydro-3-hydroxy-1-methyl-5-2H-1,4-benzodiazepine-2-one
e) Lorazepam; 7-Chloro-5-(o-chlorophenyl)-1,3-dihydro-3-hydroxy-2H-1,4-benzodiazepine-2-one
f) Prazepam; 7-Chloro-1-cyclopropylmethyl-1,3-dihydro-5-phenyl-2H-1,4-benzodiazepine-2-one
g) Fludiazepam; 7-Chloro-1,3-dihydro-5-(2-fluorophenyl)-1-methyl-2H-1,4-benzodiazepine-2-one
h) Flurazepam; 7-Chloro-1-(2-(dimethylamino)ethyl)-5-(o-fluorophenyl)-1,3-dihydro-2H-1,4-benzodiazepine-2-one
i) Medazepam; 7Chloro-2,3-dihydro-1-methyl-5-phenyl-1H-5,4-benzodiazepine
j) Bromazepam; 7-Bromo-5-(2-pyridyl)-3H-1,4-benzodiazepine-2(1H)-one
k) Nitrazepam 1,3-Dihydro-7-nitro-5-phenyl-2H-1,4-benzodiazepine-2-one
l) Nimetazepam; 1-Methyl-7-nitro-5-phenyl-1,3-dihydro-2H-1,4-benzodiazepine-2-one
m) Clonazepam; 5-(o-Chlorphenyl)-7-nitro-1H-1,4-benzodiazepine-2(3H)-one
n) Flunitrazepam; 5-(o-Fluorophenyl)-1,3-dihydro-1-methyl-7-nitro-2H-1,4-benzodiazepine-2-one
o) Estazolam; 8-Chloro-1,6-phenyl-4H-s-triazolo(4,3- ) (1,4)-benzodiazepine
p) Triazolam; 8-Chloro-6-(o-chlorophenyl)-1-methyl-4H-s-triazolo(4,3- )(1,4)-benzodiazepine
q) Alprazolam; 8-Chloro-1-methyl-6-phenyl-4H-s-triazolo (4,3- )(1,4)-benzodiazepine
r) Oxazolam; 10-Chloro-2,3,5,6,7,11b-hexahydro-2-methyl-11b-phenylbenzo(6,7)-1,4-diazepino(5,4-b-oxazol-6-one
s) Cloxazolam; 10Chloro-11b-(o-chlorophenyl)-2,3,5,6,7, 11b-hexahydrobenzo(6,7)-1,4-diazepino(5,4-b)oxazol-6-one
t) Haloxazolam; 10-Bromo-11b-(o-fluorophenyl)-2,3,7,11b-tetrahydro-oxazolo(3,2,-d)(1,4)benzodiazepine-6(5H)-one Especially preferred are benzodiazepines b), e), i), k), l), n) and o).

The amount of active agent(s) blended is sufficient if it is effective for achieving the desired pharmaceutical effect, which varies depending upon the kind of active agents, body weight of the patient, symptoms, etc. The amount may thus be suitably chosen depending upon these conditions. In general, it is preferred that active agents be employed in an amount of 0.01 to 50% by weight, more preferably 0.05 to 10% by weight, based on the total amount of Component A and Component B.

The dose of the active agents administered can be controlled by increasing or decreasing the area of skin to which the pharmaceutical compositions are applied. Accordingly, the amount of the active agent is not necessarily limited to the above-described ones.

As will be apparent to one skilled in the art, with increasing concentrations of active agent increasing amounts of active agent will be absorbed by the subject. The following discussion is given in terms of blood levels of drug (ng/ml of plasma), this being dependent upon the total area of dermal application, as there is a substantially linear increase in amount of active agent absorbed with area.

For a constant area of application and a constant absolute amount of adjuvant, the blood level of active agent at any given time is a function of the concentration of active agent in the composition. That is, increased concentrations of active agent in the formulation result in more rapid active agent penetration and higher blood levels.

A further factor which must be considered is that the amount of active agent absorbed will depend on the site of application, for example, scalp, ventral forearm, behind the ear, chest, etc. Typically an area rich in blood vessels is selected.

For most applications, the concentration of active agent in the PAEC will generally be on the order of 0.01 to 50% based on Components A and B, the amount of PAEC applied will be about 0.1 mg to 100 mg per cm$^2$ and the total area of application will be on the order of about 0.5 cm$^2$ to about 100 cm$^2$, which will provide therapeutic blood levels of the desired active agent.

These ranges are not, however, to be considered as limitative.

In general, the rate of transepidermal active agent absorption will approach the rate of oral absorption depending upon the factors previously discussed (nature and amount of PAEC, concentration of active agent in the formulation, and surface area of skin application). Thus, peak blood levels of the active agent may be reached more slowly or at about the same rate and will reach about the same level as those obtained by oral administration. Alternatively, the blood level of active agent attained by single dose oral administration may be maintained for an extended period by subsequent percutaneous administration of the active agent. In the latter case, the initial oral dose may be smaller than the normal therapeutic oral dose so that side effects associated with higher-than-minimal therapeutic blood levels attained by a reduced oral dose may be maintained by the subsequent transepideraml administration at a proper rate.

Therapeutic oral doses of diazepam in man produce blood levels of approximately 100 ng/ml plasma [S. A. Kaplan, M. L. jack, K. Alexander, and R. E. Weinfield, J. Pharm. Sci., 62, 1789-1796 (1973)]. Such a blood level is easily attainable by percutaneous administration by way of the present invention and produces pharmacological (behavioral) signs of therapeutic effectiveness in appropriate animal models for man, e.g., the rhesus monkey.

The method of the present invention finds application with mammals in general, most particularly man and domestic animals such as cows, sheep, horses, dogs, cats and the like.

The pharmaceutical composition of the present invention is administered to the outer skin as a simple mixture or as a medical preparation by adding known pharmaceutically acceptable third components in the form of solutions, ointments (paste-including creams and gels) lotions, adhesive tapes, a plaster, etc.

For example, solutions may simply comprise the active agent dissolved in the PAEC with optional components, e.g., glycerin, and the solutions may be incorporated into absorbents, e.g., a gauze, porous membrane, etc.

Ointments, gels or creams may contain conventional ingredients (e.g., polyethylene glycol and hydroxy propylcellulose, etc.) to form the same, and the same may be spread onto backing materials, e.g., a plastic film.

Similarly, plasters or adhesives tapes may contain the active agent and PAEC in an adhesive base, e.g., acrylic copolymers or other synthetic gums.

The above listed components should essentially be inert in the system and not increase or decrease the effect of the PAEC.

The PAEC may be added to such a composition in varying amounts as desired, generally from 10 to 99% by weight.

In developing the present invention, we used both diffusion cells and an animal model. The diffusion cell methods provided a qualitative assessment of the active agent/PAEC effect on percutaneous absorption. The animal model rhesus monkey test also provides an acceptable pharmacokinetic model for man as indicated in J. Soc. Cosmet. Chem., 30, 297-307. Sep./Oct. 1979 and Toxicol. Appl. Pharmacol., 32, 394-398, 1975.

EXPERIMENTAL

In Vitro Skin Penetration Studies with Diffusion Cell Technique

Rat full thickness skins were used in the diffusion cell method of Michaels, AIChE Journal, 21 [5], 985-996, 1975. The rat skin was mounted in the diffusion cell in a vertical position between the upstream and the downstream compartments; the exposed area of the skin approximated 4.15 cm$^2$.

The skin was excised from the shaved abdominal site of male albino rats weighing 150~300 g, and washed with normal saline solution after the subcutaneous fat was carefully removed with scissors.

The active agent/PAEC solution of known concentration was added to the upper compartment of the cell, which was exposed to the epithelial side of the skin and a normal saline solution was placed in the lower compartment.

The penetration rate was studied in a thermostated bath at 30° C. At appropriate intervals samples were withdrawn from the lower compartment and subsequently analyzed for active agent concentration by standard analytical methods.

As an alternative, the finite dose technique of Franz, Curr. Probl. Dermatol., Vol. 7, p. 58~68 (Karger, Basel, 1978) can also be followed where the rat skin is mounted horizontally in a diffusion cell apparatus and the exposed area of the skin approximates 0.7 cm$^2$.

The active agent/PAEC solution of known concentration was added to the upstream compartment to which the epithelial side of the skin was exposed, and a normal saline solution was added to the downstream compartment.

In Vivo Rhesus Monkey Test

If desired, an in vivo rhesus monkey test as described below can also be used to determine the effect of the PAEC/diol moderator combinations of the present invention.

Male rhesus monkeys weighting 10-14 Kg can be used as the subject. An appropriate area of the monkey's chest is shaved 24 hours before drug application.

Drug formulations comprising the PAEC are applied to a certain area of the chest. The monkey is restrained in a chair to prevent it from touching its chest.

Blood samples are taken at appropriate intervals after the application. The heparinized blood is centrifuged, and the plasma removed and stored at $-20°$ C. until analyzed.

Diazepam in plasma can be analyzed following the GLC method of Aingales, J. Chromatog., 75, 55-78, 1973.

Hereafter the present invention will be illustrated with reference to an example in more detail, but it is not to be deemed to be limited thereto.

Examples of certain combinations of Components A and B per the present invention are given in Counsel's Reference A-4271 filed May 20, 1983, and assigned U.S. Ser. No. 496,732 in the names of S. Satoh et al and entitled METHOD FOR PERCUTANEOUSLY ADMINISTERING PHYSIOLOGICALLY ACTIVE AGENTS wherein no diol and/or triol moderator is used, and in Counsel's Reference A-4556 filed Jul. 1, 1983 and assigned U.S. Ser. No. 510,133 in the names of K. Saito et al and entitled METHOD FOR PERCUTANEOUSLY ADMINISTERING PHYSIOLOGICALLY ACTIVE AGENTS USING AN ALCOHOL ADJUVANT AND A SOLVENT.

Compositions were prepared by firstly dissolving Component A with Component B, then mixing the active agent in the mixture and then mixing the diol and/or triol therein. The order of mixing is not important. In the case that Component B is a solid at ambient temperature or will not homogenously mix with Component A, 20 wt. % of ethylene glycol monobutyl ether based on the weight of Components A and B was used as an agent for assisting dissolution.

Further, in the following example, the abbreviations below are used:

$C_{12}OH$—dodecanol
$C_{12}Cl$—dodecyl chloride
DMAc—dimethyl acetamide
MP—1-methyl-2-pyrrolidone Unless otherwise indicated, in the following examples the active agent was diazepam or metoclopramide hydrochloride. The flux of the active agent is given in the terms of μg/cm²/8 hours. 25 Volume percent component A with respect to component A and component B volume with or without diols and/or triols was used in the composition along with 2.5 weight percent of the active agent. For purposes of comparison, in one instance the result for an adjuvant alone with a diol and/or triol is given.

EXAMPLE 1

Figure 1:
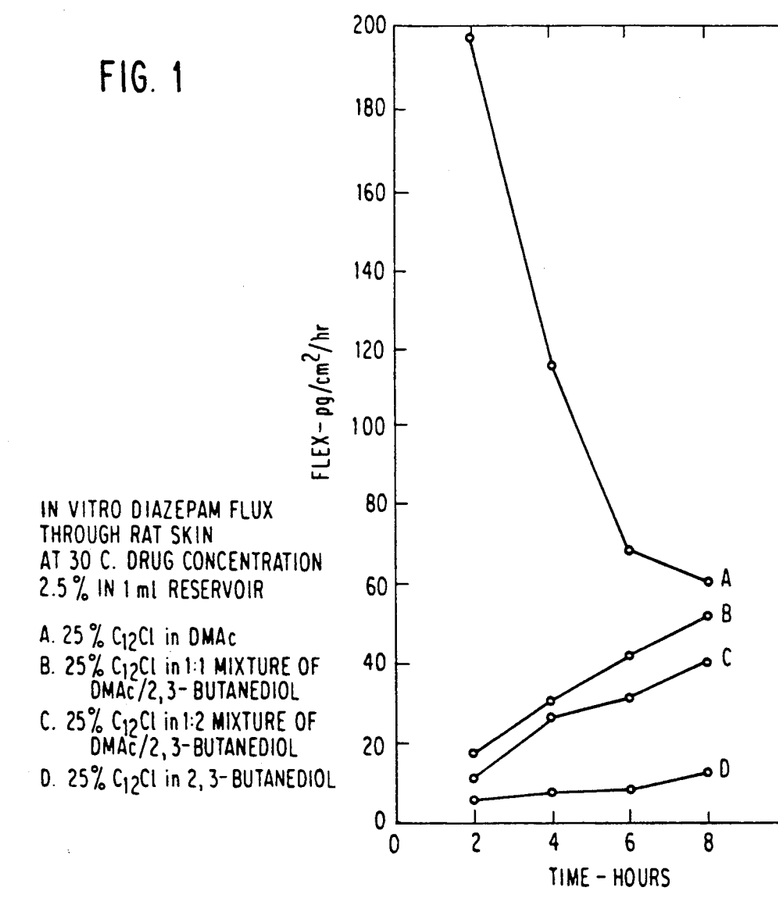
FIG. 1 is a plot of diazepam flux versus time in hours for various inventive and comparison compositions.

FIG. 1 is a plot of a diazepam flux versus time (in hours) illustrating the moderating effect of diols for the systems 25% $C_{12}Cl$ in DMAc, 25% $C_{12}Cl$ in a 1:1 weight mixture of DMAc/2,3-butane diol and 25% $C_{12}Cl$ in a 1:2 weight mixture of DMAc/2,3-butane diol. 25% $C_{12}Cl$ in 2,3-butane diol is also shown for comparison.

EXAMPLE 2

This example shows the moderating effect of diols for the system 25% $C_{12}OH$ in MP and 75% decyl oleate in MP. 1,2-propanediol was used as a diol moderator. Table 1 show the metoclopramide.HCl relative flux for 8 hours with these systems.

TABLE 1

| | | Relative Flux |
|---|---|---|
| System: | 25% $C_{12}OH$ in MP | as 1.0 |
| | 25% $C_{12}OH$ in a 1:1 volume mixture of MP/1,2-propanedol | 0.41 |
| | 25% $C_{12}OH$ in a 1:2 volume mixture of MP/1,2-propanediol | 0.21 |
| System: | 75% decyl oleate in MP | as 1.0 |
| | 75% decyl oleate in a 1:1 volume mixture of MP/1,2-propanediol | 0.75 |

EXAMPLE 3

This example show in vivo plasma metoclopramide.HCl levels with a topical gel formulation.

200 mg of metoclopramide.HCl was dissolved in 4 ml of 10% $C_{12}OH$ in a 1:1 volume mixture of MP/1,2-propanediol. To this solution was added 160 mg of Klucel (hydroxypropylcellulose type HF; Hercules Inc.) and the same stirred thoroughly to obtain a uniform gel. 1.0 ml of the gel was applied to 49 cm² of the chest area of the rhesus monkey; the applied area was left open to the air during the experiment.

The results are shown in Table 2.

TABLE 2

| Hours after application | 1 | 2 | 3 | 5 | 7 |
|---|---|---|---|---|---|
| Metoclopramide.HCl plasma levels (ng/ml of plasma) | 75 | 146 | 178 | 121 | 93 |

EXAMPLE 4

This example shows the moderating effect of 1,2-propanediol on theophylline flux through rat skin with the system 25% $C_{12}OH$ in MP. 400 mg of theophylline was mixed in 1 ml of each system.

Table 3 shows the theophylline relative flux for 8 hours with these systems.

TABLE 3

| | Relative Flux |
|---|---|
| 25% $C_{12}OH$ in MP | as 1.0 |
| 25% $C_{12}OH$ in a 1:1 volume mixture of MP/1,2-propanediol | 0.81 |

EXAMPLE 5

This example shows the moderating effect of the triols on the system 5% 5-decanol in MP and 5% 4-octanol in MP. Glycerol was used as the triol moderator. 100 mg of metoclopramide.HCl in 1 ml of these systems was used.

Table 4 shows the metoclopramide.HCl relative flux for 8 hours with these systems.

TABLE 4

| | | Relative Flux |
|---|---|---|
| System: | 5% 5-decanol in MP | as 1.0 |
| | 5% 5-decanol in a 1:1 volume mixture of MP/glycerol | 0.43 |
| System: | 5% 4-octanol in MP | as 1.0 |
| | 5% 4-octanol in a 1:1 volume mixture of MP/glycerol | 0.55 |

Figure 2:
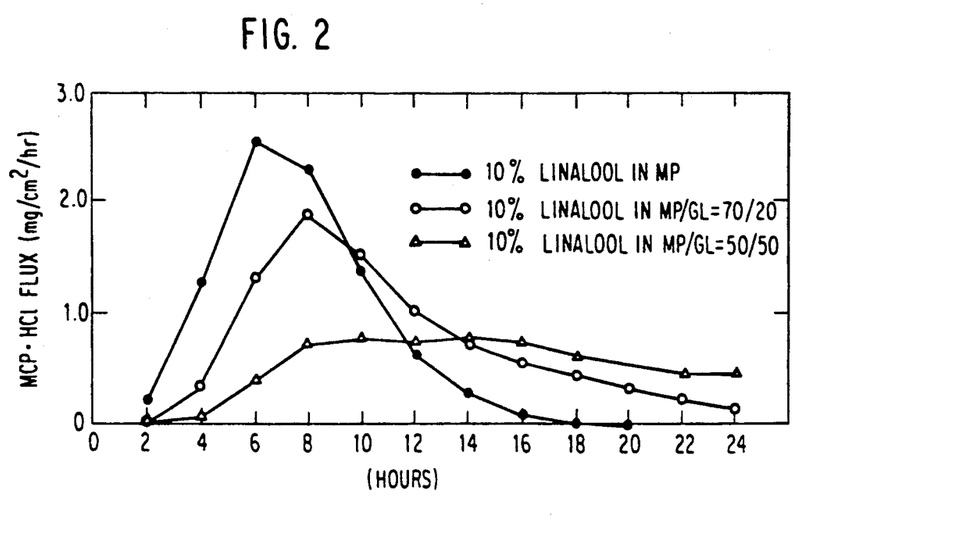
FIG. 2 is a plot of metaclopramide.HCl flux versus time illustrating the moderating effect of a triol.

FIG. 2 is a plot of metaclopramide.HCl flux versus time illustrating the moderating effect of a triol for the system 10 volume % linaolool (a $C_{10}$ branched and unsaturated higher monoalcohol) in 1-methyl-2-pyrrolidone (MP), 10 volume % linalool in a 70:20 volume mixture of MP/glycerol and 10 volume % linalool in a 50:50 volume mixture of MP/glycerol, al percents being based on total volume.

In the following Examples 6, 8, 9, 11 and 12, in vitro transdermal penetration was again analyzed followed the method of Michaels, AIChE Journal, 21, [5], pp. 985–996 (1975), according to the earlier described procedure. The sample volume was 1 ml unless otherwise indicated and flux of the active agent is given in μg/cm²/8 hours. Al percents are volume percents based on the total volume of the system unless otherwise indicated.

In Examples 7 and 10, in the in vivo Rhesus monkey test earlier described was followed except for modifying as described in Example 7.

EXAMPLE 6

This Example illustrates the moderating effect of the diol 1,2-propanediol on the flux of various non-steroidal antiinflammatory drugs (NSAIDs) with various systems comprising Component A and Component B.

25 mg of the NSAID, Indomethacin, Diclofenac sodium or Ibuprofen in 1 ml of various systems were used. The following Table shows the relative flux of the NSAID for 8 hours with the recited systems.

TABLE 5

| | Relative Flux |
|---|---|
| (Indomethacine) | |
| 25% $C_{12}OH$ in MP | as 1.0 |
| 25% $C_{12}OH$ in a 2:1 volume mixture of MP/1,2-propanediol | 0.73 |
| (Diclofenac) | |
| 25% ethyl laurate in MP | as 1.0 |
| 25% ethyl laurate in a 2:1 volume mixture of MP/1,2-propane diol | 0.61 |
| (Ibuprofen) | |
| 25% $C_{12}OH$ in N-methyl piperidone | as 1.0 |
| 25% $C_{12}OH$ in a 2:1 volume mixture of N-methyl piperidone/1,2- | 0.48 |

TABLE 5-continued

|  | Relative Flux |
| --- | --- |
| propanediol |  |

EXAMPLE 7

This Example illustrates in vivo plasma indomethacin level with a topical formulation.

49 cm² of a polyester non-woven cloth (230 mg) impregnated with 1 ml of 25% $C_{12}OH$ in a 2:1 volume mixture of MP/1,2-propanediol containing 200 mg of Indomethacin was applied to the upper back of a rhesus monkey; the applied area was occluded with Saran ® film.

The plasma level of Indomethacine was analyzed by conventional HPLC.

The results were:

| Hours after application | 1 | 3 | 5 | 7 |
| --- | --- | --- | --- | --- |
| Indomethacin plasma level (ng/ml of plasma) | 619 | 452 | 388 | 429 |

EXAMPLE 8

This Example illustrates the moderating effect of a triol, glycerol, on the flux of an NSAID, diclofenac sodium, using the system 25% $C_{12}OH$ in MP.

25 mg diclofenac sodium in 1 ml of the system was used.

The following Table shows the relative flux of diclofenac sodium for 8 hours with this system.

TABLE 6

|  | Relative Flux |
| --- | --- |
| 25% $C_{12}OH$ in MP | as 1.0 |
| 25% $C_{12}OH$ in a 2:1 volume mixture of MP/glycerol | 0.57 |

EXAMPLE 9

This Example illustrates the moderating effect of 1,2-propanediol on propranolol flux through rat skin with the system 25% $C_{12}OH$ in MP and 25% ethyl laurate in MP.

25 mg of propranolol HCl, a Beta-blocker, was mixed in 1 ml of each system.

The Table below shows the propranolol relative flux for 8 hours with these systems.

TABLE 7

|  |  | Relative Flux |
| --- | --- | --- |
| System: | 25% $C_{12}OH$ in MP | as 1.0 |
|  | 25% $C_{12}OH$ in a 2:1 volume mixture of MP/1,2-propanediol | 0.56 |
| System: | 25% ethyl laurate in MP | as 1.0 |
|  | 25% ethyl laurate in a 2:1 volume mixture of MP/1,2-propanediol | 0.34 |

EXAMPLE 10

The in vivo procedure of Example 7 was duplicated except for using propranolol as the active agent in place of the NSAID used, e.g., Indomethacin.

The results were:

| Hours after application | 1 | 3 | 5 | 7 |
| --- | --- | --- | --- | --- |
| Propranolol plasma level (ng/ml of plasma) | 30 | 115 | 130 | 90 |

EXAMPLE 11

This Examples illustrates the moderating effect of glycerol on the system 25% 3-octanol in MP.

25 mg of Pindolol, a Beta-blocker, was mixed in 1 ml of the systems below.

The Table below shows the Pindolol relative flux for 8 hours with these systems.

TABLE 8

|  | Relative Flux |
| --- | --- |
| 25% 3-octanol in MP | as 1.0 |
| 25% 3-octanol in a 2:1 volume mixture of MP/1,2-propanediol | 0.34 |

EXAMPLE 12

This Example illustrates the moderating effect of 1,2-propanediol on Verapamil flux with the system 25% $C_{12}OH$ in MP and the system 25% ethyl laurate in MP.

25 mg of Verapamil, a calcium antagonist, was mixed in 1 ml of these systems.

1 ml of 25% $C_{12}OH$ in 1,2-propanediol and 1 ml of dimethyl sulfoxide (DMSO) containing 25 mg Verapamil are shown for comparison.

The Table below shows the Verapamil relative flux for 8 hours with these systems.

TABLE 9

|  |  | Relative Flux |
| --- | --- | --- |
| System: | 25% $C_{12}OH$ in MP | as 1.0 |
|  | 25% $C_{12}OH$ in a 2:1 volume mixture of MP/1,2-proanediol | 0.60 |
|  | 25% $C_{12}OH$ in 1,2-propanediol (Control) | 0.13 |
|  | Dimethyl sulfoxide (DMSO) (Background) | 0.02 |
| System: | 25% ethyl laurate in MP | as 1.0 |
|  | 25% ethyl laurate in a 2:1 volume mixture of MP/1,2-propanediol | 0.36 |
|  | Dimethyl sulfoxide (DMSO) (Background) | 0.02 |

While there have been described what are at present considered to be the preferred embodiments of this invention, it will be obvious to those skilled in the art that various changes and modifications can be made therein without departing from the invention, and it is, therefore, intended to cover all such changes and modifications as fall within the true spirit and scope of the invention.

What is claimed is:

1. A method for percutaneously administering a physiologically active agent to a mammal which comprises applying the physiologically active agent to the skin of the mammal in a mixture consisting essentially of i) at least one of the following Components A, ii) at least one of the following Components B and iii) at least one member selected from the group consisting of diols, triols and mixtures thereof which reduces the rate of percutaneous absorption of the physiologically active agent in the mixture as compared to an otherwise identical mixture without the member selected from the group consisting of diols, triols and mixtures thereof

Component A: an alcohol ester of an aliphatic carboxylic acid having a total number of carbon atoms of from 7 to 18 having a melting point below 38° C., an aliphatic monoalcohol having from 8 to 26 carbon atoms having a melting point below 38° C. and mixtures thereof;

Component B: a compound represented by the formula:

wherein $R_5$ represents a hydrogen atom or a lower alkyl group having 1 to 4 carbon atoms, $R_6$ represents a hydrogen atom and n represents an integer of 3 to 5, wherein Components A and B are present in an amount effective to enhance percutaneous administration of the active agent and the member selected from the group consisting of diols, triols and mixtures thereof is present in an amount effective to reduce the rate of percutaneous absorption as compared to an otherwise identical mixture without the diols, triols and mixtures thereof, the rate of reduced percutaneous absorption being within the range of therapeutically effective rates.

2. The method of claim 1, wherein said alcohol ester of an aliphatic carboxylic acid is a fatty acid ester represented by the formula $R_{10}COOR_{11}$ wherein the total number of carbon atoms in $R_{10}$ and $R_{11}$ is from 10 to 17, wherein said aliphatic monoalcohol has from 8 to 20 carbon atoms, and wherein said compounds represented by the formula has the formula:

where n is 3 to 5, $R_{12}$ is an alkyl group containing from 1 to 4 carbon atoms and $R_{13}$ is a hydrogen atom.

3. The method of claim 1, wherein said Component A is said alcohol ester of an aliphatic carboxylic acid.

4. The method of claim 1, wherein said Component A is said aliphatic monoalcohol.

5. The method of claim 3 wherein said diol has 3 to 8 carbon atoms.

6. The method of claim 3 wherein said diol is an aliphatic diol having 3 to 6 carbon atoms.

7. The method of claim 3 wherein said triol is an aliphatic triol having 3 to 6 carbon atoms.

8. The method of claim 3 wherein said triol is glycerol.

9. The method of claim 3, wherein said member from said group is said diol.

10. The method of claim 3, wherein said member from said group is said triol.

11. The method of claim 4, wherein said member from said group is said diol.

12. The method of claim 4, wherein said member from said group is said triol.

13. The method of claim 1, wherein said Component A has 10 to 15 carbon atoms.

14. The method of claim 1, wherein said Component A has less than 10 carbon atoms and said member from said group is said triol.

15. The method of claim 1, wherein said Component A has more than 15 carbon atoms and said member from said group is said diol.

16. The method of claim 1, wherein the amount of the at least iii) one member selected from the group consisting of diols, triols and mixtures thereof is about 10 to about 400 wt %, based on the weight of Component B.

17. The method of claim 16, wherein the amount of the at least iii) one member selected from the group consisting of diols, triols and mixtures thereof is about 25 to about 200 wt %, based on the weight of Component B.

18. The method of claim 1, wherein Component B is 1-methyl-2-pyrrolidone.

19. The method of claim 4, wherein the amount of the at least iii) one member selected from the group consisting of diols, triols and mixtures thereof is about 10 to about 400 wt %, based on the weight of Component B.

20. The method of claim 4, wherein the amount of the at least iii) one member selected from the group consisting of diols, triols and mixtures thereof is about 25 to about 200 wt %, based on the weight of Component B.

21. A method for percutaneously administering a physiologically active agent to a mammal which comprises applying the physiologically active agent to the skin of the mammal in a mixture consisting essentially of at least one of the following i) Components A, ii) Component B which is 1-methyl-2-pyrrolidone and at least iii) one member selected from the group consisting of diols, triols and mixtures thereof which reduces the rate of percutaneous absorption of the physiologically active agent in the mixture as compared to an otherwise identical mixture without the member selected from the group consisting of diols, triols and mixtures thereof;

Components A being an alcohol ester of an aliphatic carboxylic acid having a total number of carbon atoms of from 7 to 18 having a melting point below 38° C., an aliphatic monoalcohol having from 8 to 26 carbon atoms having a melting point below 38° C. and mixtures thereof; and wherein Components A and Component B which is 1-methyl-2-pyrrolidone are present in an amount effective to enhance percutaneous administration of the active agent and the member selected from the group consisting of diols, triols and mixtures thereof is present in an amount effective to reduce the rate of percutaneous absorption as compared to an otherwise identical mixture without diols, triols and mixtures thereof, the rate of reduced percutaneous absorption being within the range of therapeutically effective rates.

22. The method of claim 21, wherein the amount of the at least iii) one member selected from the group consisting of diols, triols and mixture thereof is about 10 to about 400 wt %, based on the weight of Component B.

23. The method of claim 21, wherein the amount of the at least iii) one member selected from the group consisting of diols, triols and mixtures thereof is about 25 to about 200 wt %, based on the weight of Component B.

24. The method of claim 23 wherein said mixture consists of i) at least one of the Components A, ii) Component B which is 1-methyl-2-pyrrolidone, and iii) at least one member selected from the group consisting of diols, triols, and mixtures thereof.

25. A method for percutaneously administering a physiologically active agent to a mammal which comprises applying the physiologically active agent to the skin of the mammal in a mixture consisting essentially of at least one of the following i) Components A, ii) Component B which is N-methyl piperidone and at least iii) one member selected from the group consisting of diols, triols and mixtures thereof which reduces the rate of percutaneous absorption of the physiologically active agent in the mixture as compared to an otherwise identical mixture without the member selected from the group consisting of diols, triols and mixtures thereof;

Components A being an alcohol ester of an aliphatic carboxylic acid having a total number of carbon atoms of from 7 to 18 having a melting point below 38° C., an aliphatic monoalcohol having from 8 to 26 carbon atoms having a melting point below 38° C. and mixtures thereof; and wherein Components A and Component B which is N-methyl piperidone are present in an amount effective to enhance percutaneous administration of the active agent and the member selected from the group consisting of diols, triols and mixtures thereof is present in an amount effective to reduce the rate of percutaneous absorption as compared to an otherwise identical mixture without diols, triols and mixtures thereof, the rate of reduced percutaneous absorption being within the range of therapeutically effective rates.

* * * * *